US006455027B1

United States Patent
Barsky et al.

(10) Patent No.: US 6,455,027 B1
(45) Date of Patent: *Sep. 24, 2002

(54) METHODS AND KITS FOR IDENTIFYING DUCTAL ORIFICES IN A NIPPLE

(75) Inventors: Sanford H. Barsky, Los Angeles; Susan M. Love, Pacific Palisades; Mary L. Alpaugh, Los Angeles, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/153,564

(22) Filed: Sep. 15, 1998

Related U.S. Application Data (63) Continuation-in-part of application No. 08/931,786, filed on Sep. 16, 1997, now Pat. No. 6,168,779.

(51) Int. Cl.[7] .......................... A61B 5/00; A61K 49/00; G01N 33/53; G01N 33/574; A61M 1/00
(52) U.S. Cl. .......................... 424/9.8; 424/9.6; 424/9.1; 435/7.1; 435/7.23; 436/543; 604/28; 604/54; 604/104
(58) Field of Search ................................ 436/172, 808, 436/183, 807; 435/975, 7.1, 17.23; 424/9.1, 9.6, 9.8; 128/898, 630, 654, 807, 653.5; 604/28, 30, 54, 35, 104, 74

(56) References Cited

U.S. PATENT DOCUMENTS

| | | | | |
|---|---|---|---|---|
| 3,786,801 A | * | 1/1974 | Sartorius | 128/2 F |
| 4,775,620 A | * | 10/1988 | Cardiff et al. | 435/7 |
| 5,650,317 A | * | 7/1997 | Chang et al. | 435/371 |
| 5,728,537 A | * | 3/1998 | Silen et al. | 435/7.23 |
| 5,763,415 A | * | 6/1998 | Sukumar | 514/44 |
| 5,851,830 A | * | 12/1998 | Imam et al. | 435/7.23 |
| 6,168,779 B1 | * | 1/2001 | Barsky et al. | 424/9.2 |
| 6,221,622 B1 | * | 4/2001 | Love | 435/7.23 |
| 6,328,709 B1 | * | 12/2001 | Hung et al. | 604/74 |

FOREIGN PATENT DOCUMENTS

WO  WO 97/05898  2/1997

OTHER PUBLICATIONS

Pinkus et al. Am. J. Clin. Pathol. 85: 269–277, abstract, 1986.*
Sawaf et al. Pathol. Biol. (Paris) 40: 655–665, abstract, 1992.*
Guelstein et al. Int. J. Cancer 42: 147–153, abstract, 1988.*
Jarasch et al. Human Pathol. 19:276–289, abstract, 1988.*
Cardenosa et al. AJR Am. J. Roentgenol. 162: 1081–1087, abstract, 1994.*
Choudhury et al. Arch Surg. 124: 874–875, abstract, 1989.*
Hou et al. Radiology 195: 568–569, abstract, 1995.*
Sundstrom et al. Int. J. Biol. Markers 9: 102–108, abstract, 1994.*
Allen et al. PNAS 81: 1203–1207, abstract, 1984.*
Nagle et al. J. Histochem. Cytochem. 34: 869–881, abstract, 1986.*
Taylor–Papadimitriou et al. J. Cell Sci. 94: 403–413, abstract, 1989.*
Karesen et al. Tidsskr. Nor Laegeforen 113: 1233–1235, abstract, 1993.*
Dairkee et al. J. Natl. Cancer Inst. 80: 691–695, abstract, 1988.*
Zimmer et al, Virchows Arch. B Cell Pathol. Incl. Mol. Pathol. 49: 161–173, abstract, 1985.*
Stanec et al. Lijec Vjesn. 115: 17–20, abstract, 1993.*
Heatley et al. J. Clin. Pathol. 48: 26–32, abstract, 1995.*
Grillo et al. Ann. Chir. Gynaecol. 79 (1): 6–9, 1990.*
Osborne J. Australas Radiol. 33 (3): 266–269, 1989.*
Bjorn–Hansen R. Br. J. Radiol. 38: 947–951, 1965.*
Van Zee et al. Cancer 82: 1874–1880, May, 1998.*
Tabar et al. Radiology 149 (1): 31–38, 1983.*
Okazaki et al. Nippon Geka Gakkai Zasshi 97 (5): 357–362, 1996.*
S.H.. Barsky et al. (1996) Laboratory Investigation, Modern Pathology, Annual Meeting Abstracts, Abstract #67, p. 15A.
Fabian et al. (1993) Proc. Ann. Meet. Am. Assoc. Cancer Res., 34:A1556.
Imayama et al. (1996) Cancer, 78(6):1229–1234.
Lewis (May/Jun. 1997) Biophotonics International, pp. 27–28.
Love (1996) 15th Annual San Antonio Breast Cancer Sypmpsoium, San Antonio, TX Abstract #197, p. 180.
Love and Barsky (1996) The Lancet, 348–997–999.
Makita et al. (1991) Breast Cancer Research and Treatment, 18:179–187.
Okazaki et al. (1991) Jpn. J. Clin. Oncol., 21(3):188–193.
Petrakis (1986) Breast Cancer Research and Treatment, 8:7–19.

(List continued on next page.)

*Primary Examiner*—S. Devi
(74) *Attorney, Agent, or Firm*—Gates & Cooper LLP (57) ABSTRACT

Methods, kits, and apparatus for locating, labelling, and accessing breast ducts are described. An orifice to one or more ductal networks is marked to enhance visibility. In a first embodiment, the orifice is labelled using a specific binding substance, typically an antibody, specific for a tissue marker present on the orifice. Exemplary tissue markers include those present on the ductal epithelium, such as cytokeratins, including cytokeratin 8 and cytokeratin 18; cadhedrins, such as E cadhedrin; and epithelial membrane antigens. In a second embodiment, a dye is injected into the base of the nipple and preferentially accumulates at at least some of the orifices. Other marking techniques are also described. Marking of the ductal orifices permits reliable identification and access to each of the multiple ductal networks which may be present in an individual breast.

9 Claims, 9 Drawing Sheets

OTHER PUBLICATIONS

Petrakis (Jan./Feb. 1993) Cancer Epidemiology Biomarkers & Prevention, 2:3–10.
Petrakis (1993) Epidemiologic Reviews, 15:188–195.
Sartorius et al. (1977) W. Logan, ed., Breast Carcinoma, New York, Wiley, pp. 281–300.
Sartorius (1995) Breast Cancer Research and Treatment, 35:255–266.
Wrensch et al. (1989) Cancer Res., 49:2168–2174.
Wrensch et al. (1990) Breast Cancer Research and Treatment, 15:39–51.
Wrensch et al. (1992) Am. J. Epidemiol., 135(2):130–141.
Falardeau, M. et al., "Selective galactophorectomy for mono-orificial nipple discharge without associated mass: technique and results. Apropos of seventy–three cases!" Ann. Chi 8. 45(9):796–801, 1991.
Feige, C., "Dynamic morpho–cyto–echography and the echographic galactoscopy endo–ductal sample. Intrinsic and extrinsic markers in the detection of breast cancers," Ultrasound Med. Biol. 14:97–108, 1988.
Hou, M. F. et al., "A Simple Method of Duct cannulation and Localization for Galactography before Excision in Patients with Nipple Discharge," *Radiology*, 195(2):568–569 (1995).
Katamine, T. et al., "Determination of cancer–associated antigens in body fluid secreted from nipple," *Chemical Abstracts*, 114(9) (2 pages (Mar. 4, 1991). JP 02 280061A.

* cited by examiner

METHODS AND KITS FOR IDENTIFYING DUCTAL ORIFICES IN A NIPPLE

This application is a continuation-in-part of application Ser. No. 08/931,786, filed on Sep. 16, 1997, now U.S. Pat. No. 6,168,779, the full disclosure of which is incorporated herein by reference.

The invention disclosed in this application was made with government support under U.S. Army Medical Research Grant Nos. DAMD17-94-J-4281 and DAMD17-96-C-6117. The government may have certain rights in the this invention.

BACKGROUND OF THE INVENTION

1. Field of the Invention

The present invention relates generally to medical methods and devices for accessing body lumens and in particular to methods and apparatus for identifying ductal orifices in human breasts and accessing the ducts through the identified orifices.

Breast cancer is the most common cancer in women, with well over 100,000 new cases being diagnosed each year. Even greater numbers of women, however, have symptoms associated with breast diseases, both benign and malignant, and must undergo further diagnosis and evaluation in order to determine whether breast cancer exists. To that end, a variety of diagnostic techniques have been developed, the most common of which are surgical techniques including core biopsy and excisional biopsy. Recently, fine needle aspiration (FNA) cytology has been developed which is less invasive than the surgical techniques, but which is not always a substitute for surgical biopsy.

A variety of other diagnostic techniques have been proposed for research purposes. Of particular interest to the present invention, fluids from the breast ducts have been externally collected, analyzed, and correlated to some extent with the risk of breast cancer. Such fluid collection, however, is generally taken from the surface of the nipple and represents fluid from the entire ductal structure or from a single duct which is spontaneously discharging. In either case, information on the condition of a preselected individual duct is generally not provided. Information on individual ducts can be obtained through cannulation and endoscopic examination, but such examinations have been primarily in women with nipple discharge or for research purposes and have generally not provided for examination of each individual duct in the breast.

Since breast cancer usually arises from a single ductal system and exists in a precancerous state for a number A of years, endoscopy in and fluid collection from individual breast ducts holds great diagnostic and therapeutic promise. Much of the promise, however, cannot be realized until identification of and access to each and every duct in a patient's breast can be assured. Presently, ductal access may be obtained by a magnification of the nipple and identification of ductal orifice(s) using conventional medical magnifiers, such as magnification loupes. While such magnified examination is relatively simple, it cannot be relied on to identify all orifices. Moreover, the ductal orifices can be confused with other tissue structures, such as sebaceous glands and simple keratin-filled caruncles of the nipple. Thus, before ductal techniques can be further developed for diagnosis, therapy, research, or other purposes, it will be useful to provide methods and apparatus which facilitate identification of ductal orifices to distinguish them from other nipple surface features, and allow subsequent ductal access in selected and/or all ducts in each breast.

2. Description of the Background Art

Publications by the inventors herein relating to breast duct access include Love and Barsky (1996) Lancet 348: 997-999; Love (1992) "Breast duct endoscopy: a pilot study of a potential technique for evaluating intraductal disease," presented at 15th Annual San Antonio Breast Cancer Symposium, San Antonio, Tex., Abstract 197; Barsky and Love (1996) "Pathological analysis of breast duct endoscoped mastectomies," Laboratory Investigation, Modern Pathology, Abstract 67. A description of the inventors' breast duct access work was presented in Lewis (1997) Biophotonics International, pages 27–28, May/June 1997.

Nipple aspiration and/or the introduction of contrast medium into breast ducts prior to imaging are described in Sartorius (1995) Breast Cancer Res. Treat. 35: 255–266; Satorious et al. (1977) "Contrast ductography for the recognition and localization of benign and malignant breast lesions: An improved technique," in: Logan (ed.), Breast Carcinoma, New York, Wiley, pp. 281–300; Petrakis (1993) Cancer Epidem. Biomarker Prev. 2: 3–10; Petrakis (1993) Epidem. Rev. 15: 188–195; Petrakis (1986) Breast Cancer Res. Treat. 8: 7–19; Wrensch et al. (1992) Am. J. Epidem. 135: 130–141; Wrensch et al. (1990) Breast Cancer Res. Treat. 15: 39–51; and Wrensch et al. (1989) Cancer Res. 49: 2168–2174. The presence of abnormal biomarkers in fine needle breast aspirates is described in Fabian et al. (1993) Proc. Ann. Meet. Am. Assoc. Cancer Res. 34: A1556. The use of a rigid 1.2 mm ductoscope to identify intraductal papillomas in women with nipple discharge is described in Makita et al. (1991) Breast Cancer Res. Treat. 18: 179–188. The use of a 0.4 mm flexible scope to investigate nipple discharge is described in Okazaki et al. (1991) Jpn. J. Clin. Oncol. 21: 188–193. The detection of CEA in fluids obtained by a nipple blot is described in Imayama et al. (1996) Cancer 78: 1229–1234. Delivery of epithelium-destroying agents to breasts by ductal cannulation is described in WO 97/05898.

SUMMARY OF THE INVENTION

The present invention provides improved methods, kits, and other apparatus for locating breast ducts in the breasts of human patients. In particular, the methods of the present invention permit reliable identification of the orifices within the nipple of a breast, where individual orifices lead to each of the multiple ductal networks within the breast. By reliably identifying each orifice, all of the ductal networks can be located and subsequently accessed for diagnostic, risk assessment, therapeutic, research, or other purposes.

Broadly, the present includes a wide variety of techniques for transiently marking and locating individual orifices in a nipple of a breast, usually a human breast. By "marking," it is meant that a substance, label, energy, or stimulus is applied to the nipple to cause labelling, a reaction, or other response which permits or enhances distinguishing an orifice from surrounding tissue in the nipple. Usually, but not necessarily, the methods will result in the marking of all orifices in a nipple to permit subsequent access to all or selected one(s) of the ductal networks associated with the orifices. The marking will be "transient," e.g. will not be permanent but instead will remain visible or otherwise detectable for a time sufficient to permit subsequent access to the associated ductal lumens, usually for a period of at least 15 minutes, preferably for about 1 to 2 hours. For the most part, the present invention will rely on introducing a detectable substance, such as a labelling reagent, dye, or the like, to the nipple so that the substance localizes and/or accumulates at or near the orifice to permit visual, automated, or other detection. Alternatively, the present invention can utilize other stimuli for inducing a response, change, or reaction at or near a location of the orifice in the nipple. For example, it may be possible to illuminate the nipple with certain light or other energies which help distinguish between the orifice and other tissue surfaces. It may also be possible to introduce chemical reagents which react with ductal secretions at the orifice to enhance visibility e.g. to produce a visible or otherwise detectable reaction product.

In a first aspect of the present invention, a method for locating an orifice of a breast duct comprises labelling ductal cells disposed at the ductal orifice with a visible or otherwise detectable label. The orifice may then be located based on the presence of the label at the orifice. Specific and preferred methods for labeling the orifices are described below in connection with a second aspect of the present invention. After the orifices have been located, an access device, such as a guidewire, catheter or fiberoptic viewing scope, can be introduced through at least one of the orifices and into the associated breast duct. The method may further comprise introducing the same or a different access device through other orifices, often into each of the orifices to permit diagnosis, treatment, or other evaluation of all of the ductal networks of a breast.

An exemplary labelling method includes treating a nipple to expose tissue in an orifice of each duct. The treated nipple is then exposed to a labelling reagent capable of specifically binding to a tissue marker characteristic of tissue at the ductal orifice. Binding of the labelling reagent to the tissue results in immobilization of a label at the orifice, permitting subsequent location of the orifice as described above. The treating step preferably comprises washing the nipple with a keratinolytic agent, such as 5% to 50% acetic acid (by weight), to remove keratin-containing materials which normally occlude the duct orifice and which could inhibit binding of the labelling reagent to the tissue marker. The tissue marker is typically characteristic of the ductal epithelium and represents either a membrane antigen or a cytoplasmic antigen. It has been found by the inventors herein that the ductal epithelium extends to within 0.1 mm to 0.2 mm of the nipple orifice and is sufficiently exposed to the surface of the nipple to permit labelling according to the methods of the present invention. Exemplary markers include cytokeratins, such as cytokeratin 8, cytokeratin 18; cadhedrins, such as E cadhedrin; epithelial membrane antigen (EMA); and the like. Usually, the labelling reagent comprises a polyclonal or monoclonal antibody or other specific binding substance specific for the marker. The antibody may be directly labelled with a visible label, such as a fluorescent label, a dye label, a chemiluminescent label, or the like. Alternatively, the labeling reagent may comprise two or more components, typically including a primary antibody which is specific for the marker and one or more secondary binding substances which bind to the primary antibody and provide a label, optionally a magnified label. For example, the primary antibody may be unlabelled, and a secondary labelled antibody specific for the primary antibody may also be provided. As a further alternative, the primary antibody can be labelled with biotin or other hapten, and binding of the label provided via avidin, secondary antibody specific for the hapten, or the like. Numerous specific techniques for labelling of antigenic tissue markers are well known and reported in the immunocytochemical staining literature.

In an alternative aspect of the present invention, one or more ductal orifices in a nipple are labelled by introducing a dye into the, usually at the base of the nipple. It is presently believed that the dye first collects in the lactiferous sinuses associated with one or more (usually all) of the ductal networks and then travels toward the surface of the nipple via a capillary mechanism through the associated ductal orifice. It is further believed that the dye localizes primarily in the ductal lumens because the cebaceous glands of the nipple do not extend fully to the base. Thus, dyes injected at the base or blow will not pass directly into the cebaceous glands. Regardless of the correctness of this presently believed mechanism, it has been found that introduction of a dye into the base of a nipple results in subsequent accumulation of the dye at at least some of and usually all of the ductal orifices. Dye labelling of all of the ductal orifices can be achieved by introducing a sufficient volume of the dye to the nipple base and/or distributing the dye evenly over the nipple base so that the dye can travel to all of the ductal lumens. Suitable dye volumes are in the range from 0.001 ml to 100 ml, preferably from 0.01 ml to 10 ml, and typically from 0.1 ml to 5 ml. In the exemplary methods, the dyes are injected using a needle and syringe, and uniform distribution of the dye over the nipple base can be enhanced-by moving the needle to slightly different locations. Usually, however, moving of the needle will not be necessary to achieve labelling of all of the ductal orifices. Suitable dyes may be colored, fluorescent, chemiluminescent, vital dyes, or the like. The dyes will be biocompatible, non-toxic, and will preferably be non-aqueous so that they are not adsorbed directly into the tissue, but rather preferentially collect within the sinuses lumens and travel to the ductal orifices. Suitable dyes include Metylene blue, Indigo carmine, Pontamine sky blue 6BX (Chicago sky blue 6B), fluorescein, Toluidine blue 0, Indocyanine green (sodium salt), Rose bengal, Patent blue violet (Patent blue), Isosulfan blue and Rhodamine B.

In another aspect, a method according to the present invention comprises marking a ductal orifice and subsequently accessing the duct through the marked orifice. Marking may comprise any of the specific methods set forth above. Accessing comprises introducing an access device through at least one of the marked orifices, and preferably through all of the marked orifices, where the access device may be a catheter, a guidewire, a fiber optic viewing scope, or the like.

In still another aspect of the present invention, a kit for labelling breast duct orifices comprises a detectable substance, such as a labelling reagent, dye, or reagents capable of specifically labelling a cellular marker at the ductal orifice, instructions setting forth a labelling method as described above, and a package containing the detectable substance and the instructions for use. Optionally, the kits of the present invention may further include the keratinolytic agent (particularly for the specific labelling protocols) and any other reagents that may be helpful or necessary for performing the method. Instructions for use will set forth the use of all provided reagents and may further set forth the use of agents which are available in the laboratory where the assay is to be performed.

In yet another aspect of the present invention, a kit for accessing a breast duct comprises a detectable substance for marking a ductal orifice. The kit further comprises an access device capable of being inserted through a marked ductal orifice to a ductal lumen, such as a catheter, a guidewire, a fiber optic viewing scope, or the like. The kit still further comprises a package containing the labelling reagent, optionally other reagents or components, and the access device. The kit may further comprise instructions for use setting forth a method comprising the accessing steps as described above.

DESCRIPTION OF THE SPECIFIC EMBODIMENTS

Figure 1:
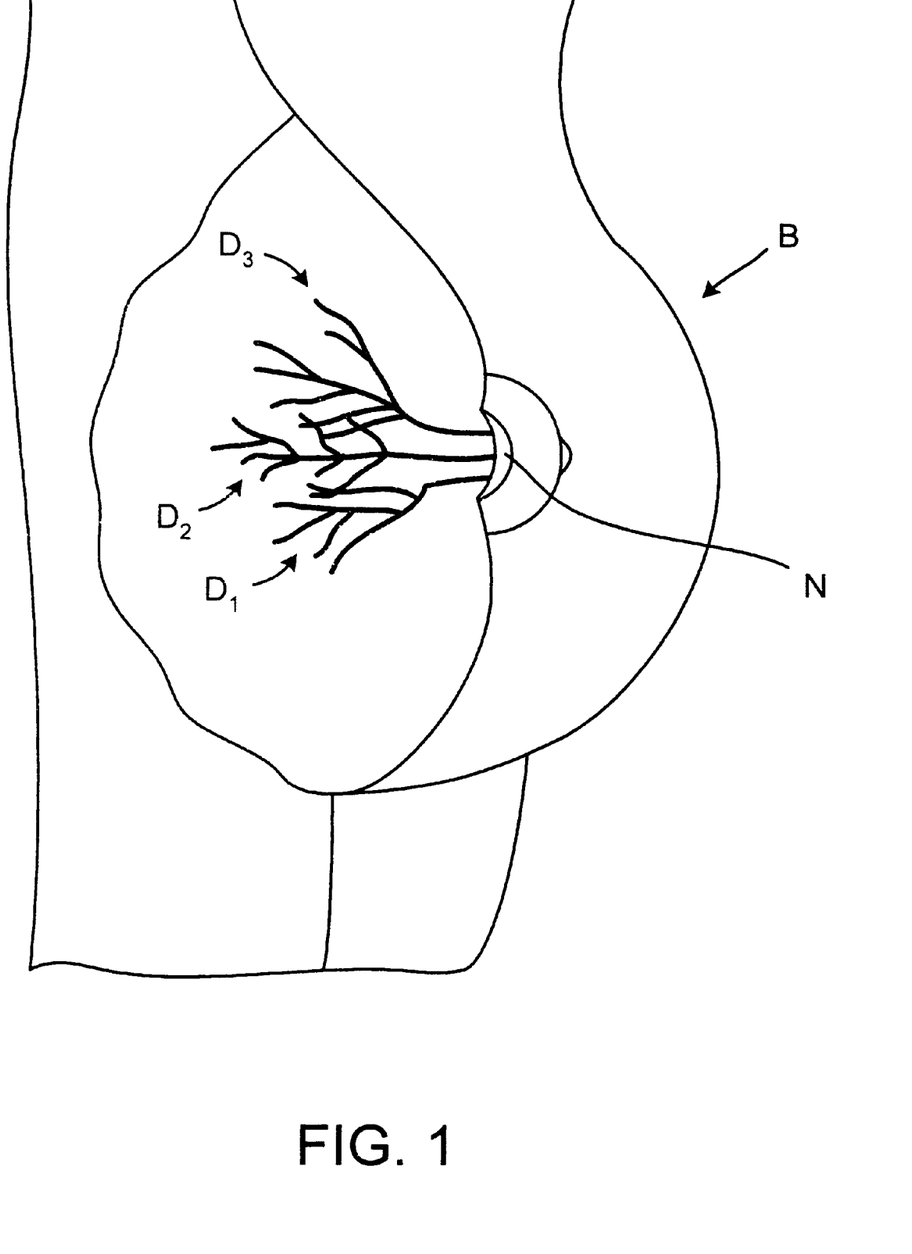
FIG. 1 is an anterior view of a human female breast, shown in section, and illustrating three of the six to nine ductal networks extending inwardly from the nipple.
Figure 2:
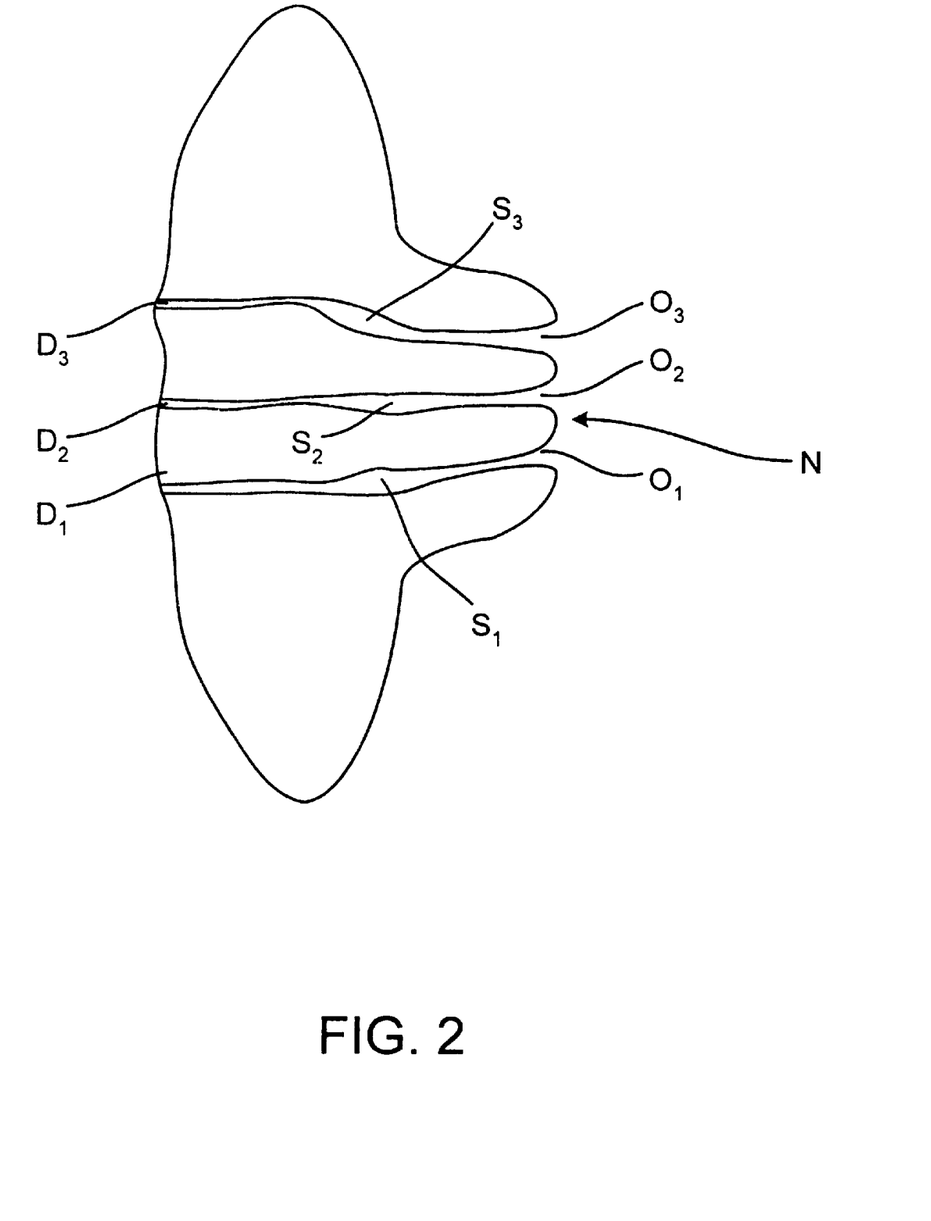
FIG. 2 is an enlarged view of the nipple of FIG. 1 ACME illustrating the orifices leading to each of the three ductal networks.

The present invention comprises methods for locating, labelling, and accessing the ductal networks in human female breasts. A typical breast B is illustrated in FIG. 1 and includes a nipple N and from six to nine ducts D. Three ductal networks $D_{1-3}$ extending inwardly from the nipple N into the breast tissue are illustrated. As best seen in FIG. 2, each ductal network $D_{1-3}$ begins with an orifice $O_{1-3}$ which lies at the surface of the nipple N and extends inwardly through a ductal sinus $S_{1-3}$ and then into a branching network. Each network D comprises a series of successively smaller lumens which are arranged in complex, three-dimensional patterns. The networks of each duct will overlap within the breast tissue but will not usually be interconnected. The present invention relies on identifying and labelling tissue in the orifice O of each duct D within the nipple N. Usually, there will be from six to nine orifices (but sometimes as many as twenty) which open into a like number of ductal networks. An abrupt transition from the ductal epithelium to the squamous epithelium of the skin is found within about 0.1 mm to 0.2 mm of the nipple surface. Typically, the ductal orifice will be occluded with a conical keratin plug measuring about 0.5 mm to 1 mm in size.

The present invention relies on marking the orifice(s) of selected one(s) or all of the ductal network(s). Marking will usually be performed by labelling the orifice or tissue adjacent to the orifice, i.e. selectively introducing a detectable substance or "label" to the orifice and/or tissue immediately surrounding the orifice so that the orifice may be distinguished from the remaining tissue surface regions of the nipple based on the presence of the substance. Such labelling may be "specific" or "non-specific." By "specific," it is meant that the label will be introduced in a manner such that it will bind to the orifice region within the nipple but not bind (or will bind to a significantly lesser extent, usually at least 10-fold less) to other regions of the nipple. In this way, binding of the label to the orifice will be a discernable indication that the orifice is present and available for access to the associated ductal network. By "non-specific," it is meant that the detectable substance is introduced to the nipple in a manner which results in accumulation of the marker at or near the orifice without specific binding or with minimal specific binding. Such non-specific labelling will usually comprise introducing a liquid dye to the base region of the nipple in a manner such that the dye will preferentially flow to and accumulate at the orifices of the nipples. The presence of the dye within the orifices allows the orifices to be distinguished from surrounding nipple tissue.

In addition to the specific and non-specific labelling techniques just described, marking according to the present invention may also comprise illuminating, stimulating, chemically reacting, or otherwise interacting with the nipple in a manner which permits or enhances the visual differences between the orifices (or tissue surrounding the orifices) and the non-orifice regions of the nipple.

In a first particular aspect of the present invention, labelling reagents will be provided which are reactive with tissue marker(s) comprising an antigenic or epitopic site characteristic of the epithelial lining of the breast duct. Surprisingly, it has been found that the epithelial lining extends sufficiently far into the orifice region of the duct to permit successful labelling using generally conventional immunocytochemical labelling reagents and techniques, as described in more detail below. Exemplary tissue markers include antigens and epitopes defined by the cytokeratins present in the epithelial cytoplasmic lining, such as cytokeratin 8, cytokeratin 18, and by molecules present in the membrane lining, such as E cadherin, epithelial membrane antigen (EMA), and the like. Suitable breast epithelial tissue markers are described, for example, in Moll et al. (1982) Cell 30:11–19; Gown and Vogel (1984) Am. J. Pathol. 114:309–321; and Johnson (1991) Cancer Metastasis Rev. 10:11–22.

Figure 3:
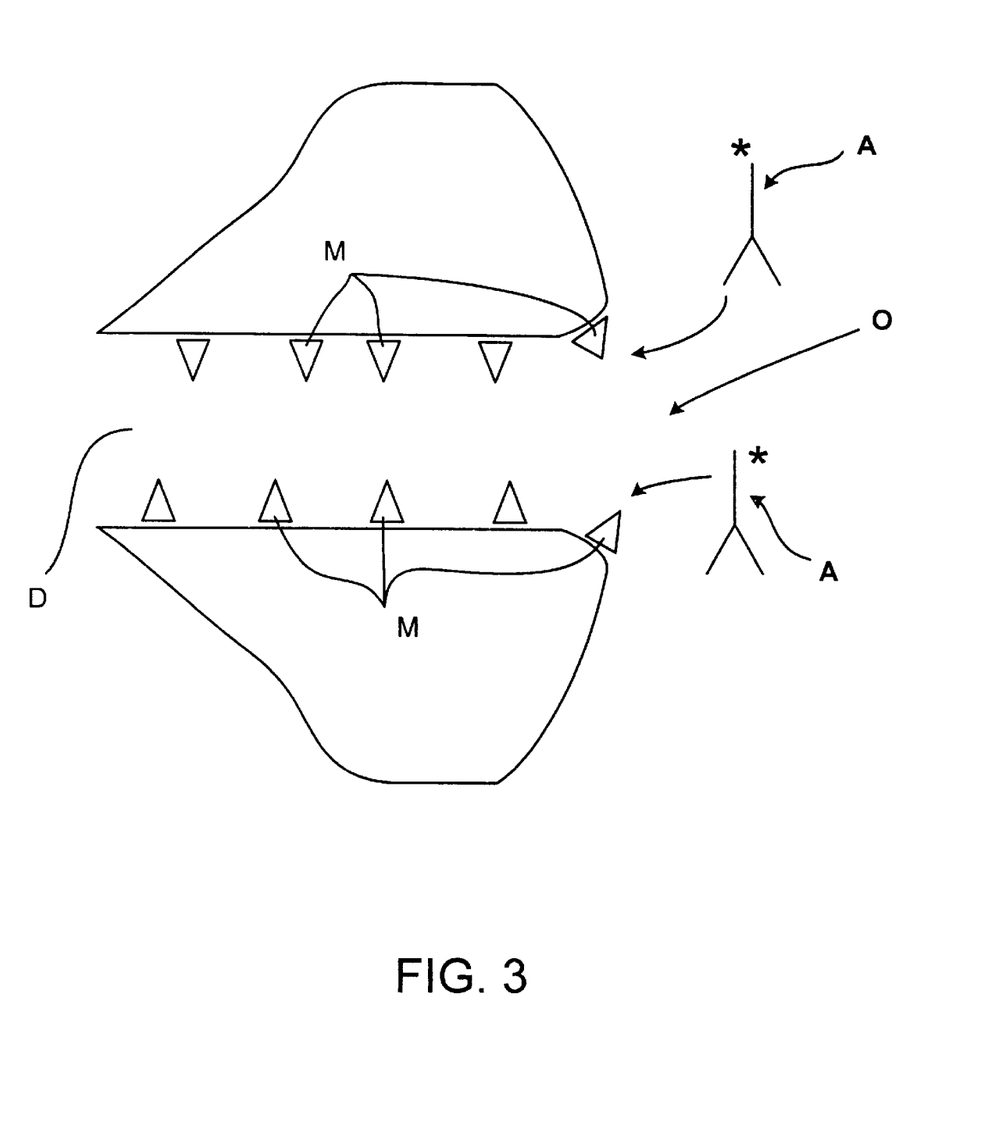
FIG. 3 is a still further enlarged view of a single orifice illustrating the distribution of tissue markers from the epithelium to the opening of the orifice, where such markers at the opening are available for binding to labelled antibodies.
Figure 4:
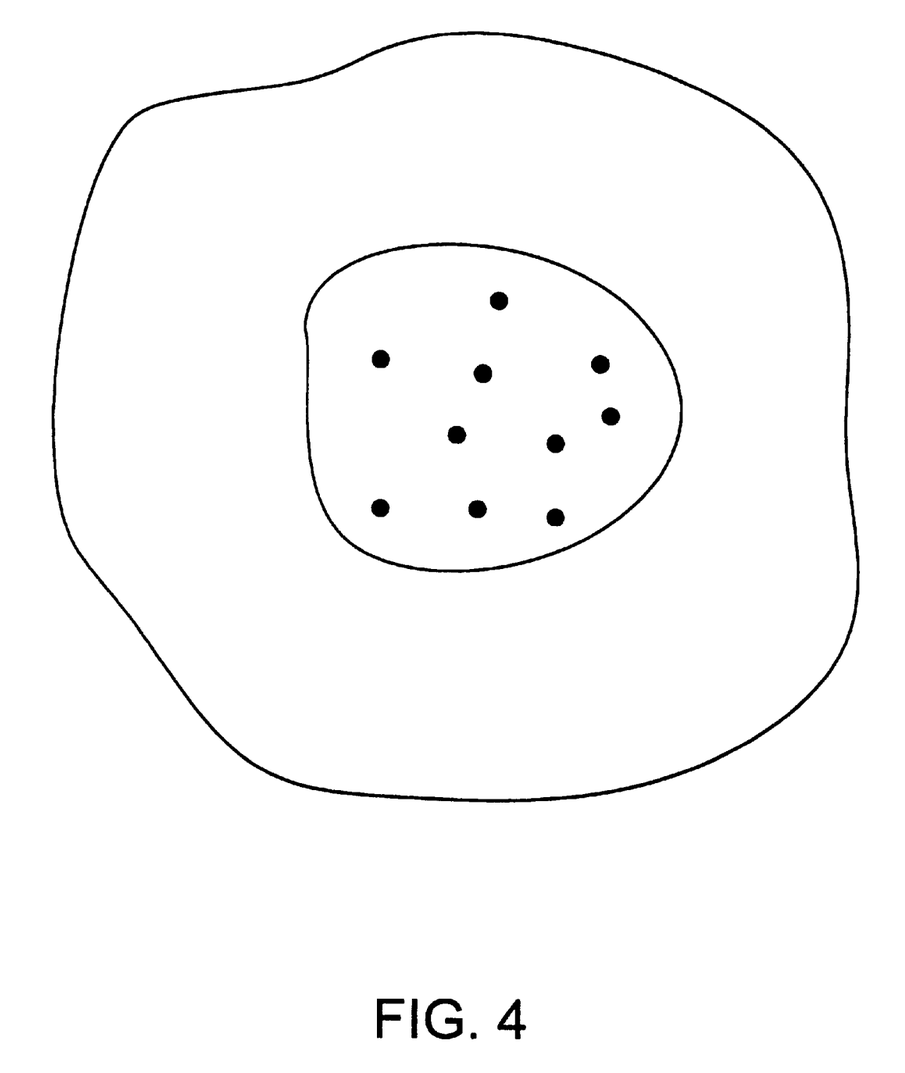
FIG. 4 is a schematic illustration of the appearance of a nipple which has been labelled with visible markers according to the methods of the present invention.

Referring now to FIG. 3, an orifice region O of a ductal network D is illustrated with a plurality of markers M lining the epithelium of the duct and extending to the perimeter of the orifice. Labelled antibodies A can be used to locate and label those markers M which are near the orifice O. Frequently, it will be desirable or necessary to wash the nipple with a solution capable of unblocking the orifice to permit binding of the antibodies or other labelling reagent. For example, the orifice can frequently become plugged with keratin-containing materials, and washing with a keratinolytic solution, such as acetic acid (5% to 50% by weight) admixed in a pharmaceutical delivery vehicle, which will expose sufficient marker sites at each orifice to enable labelling according to the methods of the present invention.

The labelled antibodies or other labelling reagents may be formulated as liquid, typically aqueous, solutions in a generally conventional manner. Suitable anti-cytokeratin antibodies may be obtained from commercial suppliers, with specific antibodies including FITC-anticytokeratin (Becton-Dickenson), CAM 5.2, and the like. The antibodies may be coupled to one member of a signal-producing system capable of generating a detectable visual or other change on the tissue surface, where an element will be referred to here and after as a "visual label." Suitable signal-producing systems include fluorescent systems, color-generating systems, and luminescent systems. Preferred is use of fluorescent systems which comprise a single fluorescent label, but other systems which comprise two or more components including enzymes, substrates, catalysts, enhancers, and the like, may also be employed. At least one component of the signal-producing system will be attached to the antibody or other specific binding substance which is capable of directly or indirectly binding to the tissue marker. Usually, the antibody will bind directly to the tissue marker, but it will also be possible to employ primary antibodies which are specific for the tissue marker and labelled secondary antibodies which introduce the label or component of the signal-producing system. For example, the primary antibody can be mouse IgG and the labelled secondary antibody can be FITC goat anti-mouse IgG (Zymed). Such signal-producing systems and the use on tissue and tissue samples is well described in the medical, scientific, and patent literature relating to immunocytochemical staining.

In an exemplary protocol according to the present invention, the nipple is first dekeratinized with 5% to 50% acetic acid to remove keratin and other potentially blocking and contaminating substances from the ductal orifices. A solution of the labelled antibody, preferably an antibody which directly binds to a cytokeratin or other epithelial cytoplasmic or surface membrane marker, such as the antibodies described above, is then applied to the nipple surface. The antibody is preferably linked to a fluorescent marker, more preferably fluorescein, and the fluorescein-labelled antibody delivered in a buffered aqueous solution. Optionally, controls may be run. For example, labelled antibodies of the same Ig class as the specific antibody may be exposed to the nipple at the same dilution. By comparing the results with the specific antibody and the control antibody, non-specific binding can be discounted.

Figure 5A:
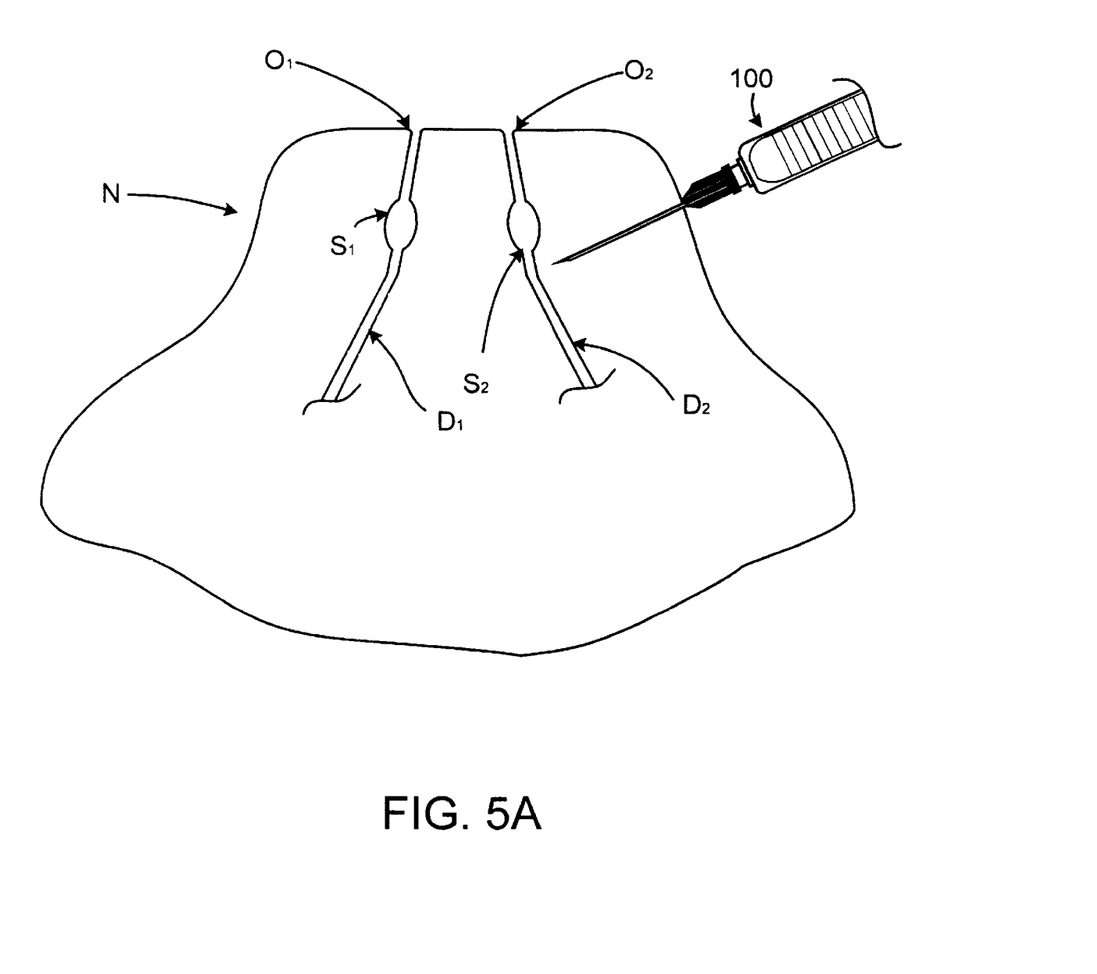
FIGS. 5A–5C illustrate a ductal marking protocol performed in accordance with the principles of the present invention.
Figure 5B:
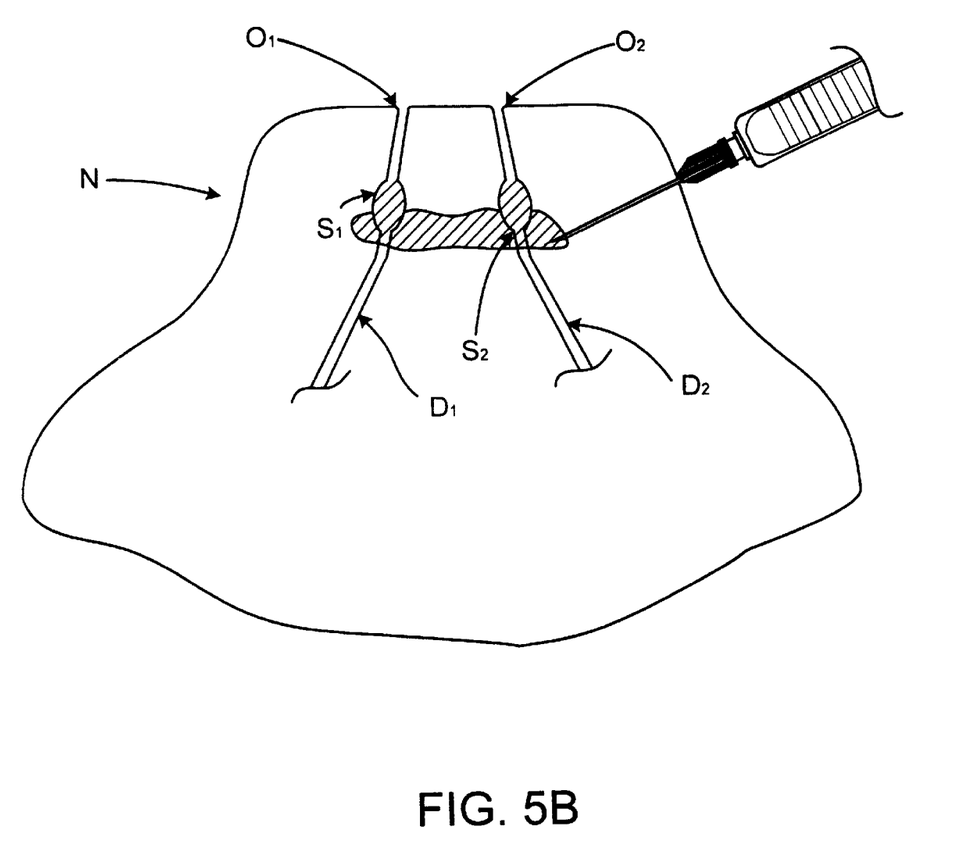
Figure 5C:
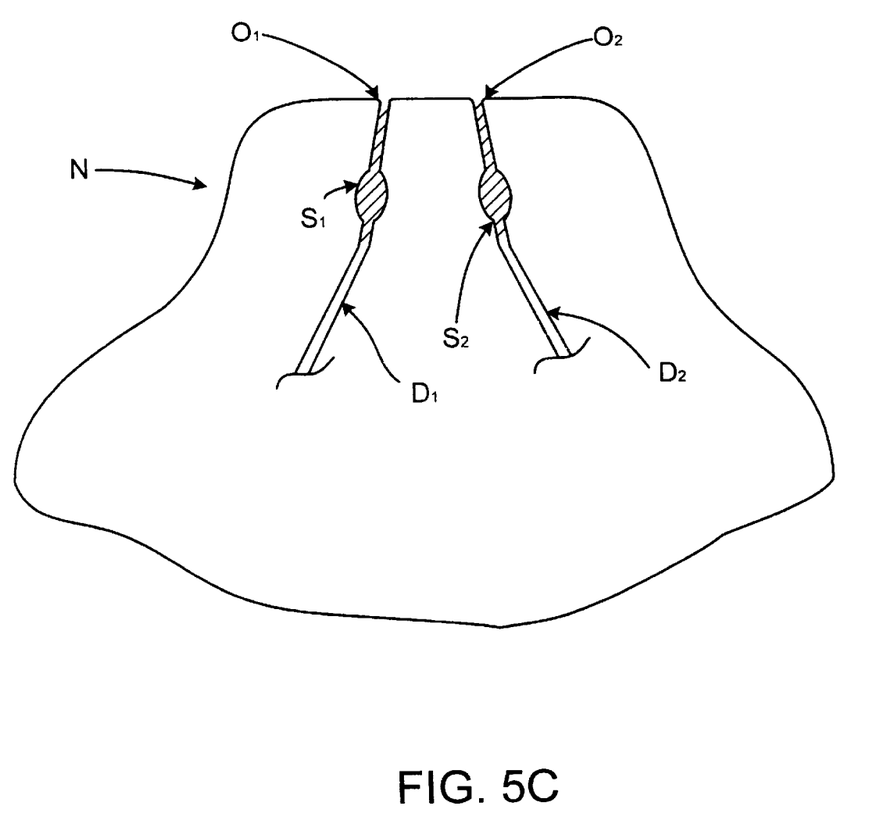

In a second particular aspect of the present invention, marking of the ductal orifices is accomplished using a dye as generally described above. With specific reference to FIGS. 5A–5C, the dye will usually be introduced to the base of a nipple N using a needle and syringe 100 or other suitable percutaneous cannula. The base of the nipple is the region between the nipple N and the main portion of breast tissue, i.e. the region where the nipple joins to the skin of the breast, and generally includes the ductal or lactiferous sinuses S as described above. A preselected volume of dye, usually within the ranges set forth above, is then injected into the base region and collects within the sinuses S, as illustrated in FIG. 5B. While only two sinuses ($S_1$ and $S_2$) are illustrated, the nipple N will typically include from 5 to 15 ductal networks, each of which include a sinus S. So long as a sufficient volume of the dye is injected, each of the sinuses will fill with a sufficient amount of dye so that the dye will travel upwardly through the ductal lumen to reach the orifice O, as illustrated in FIG. 5C. As amply demonstrated in the Experimental section hereinafter, presence of the dye at the orifice allows convenient and reliable visual detection of each of the orifices.

Figure 6:
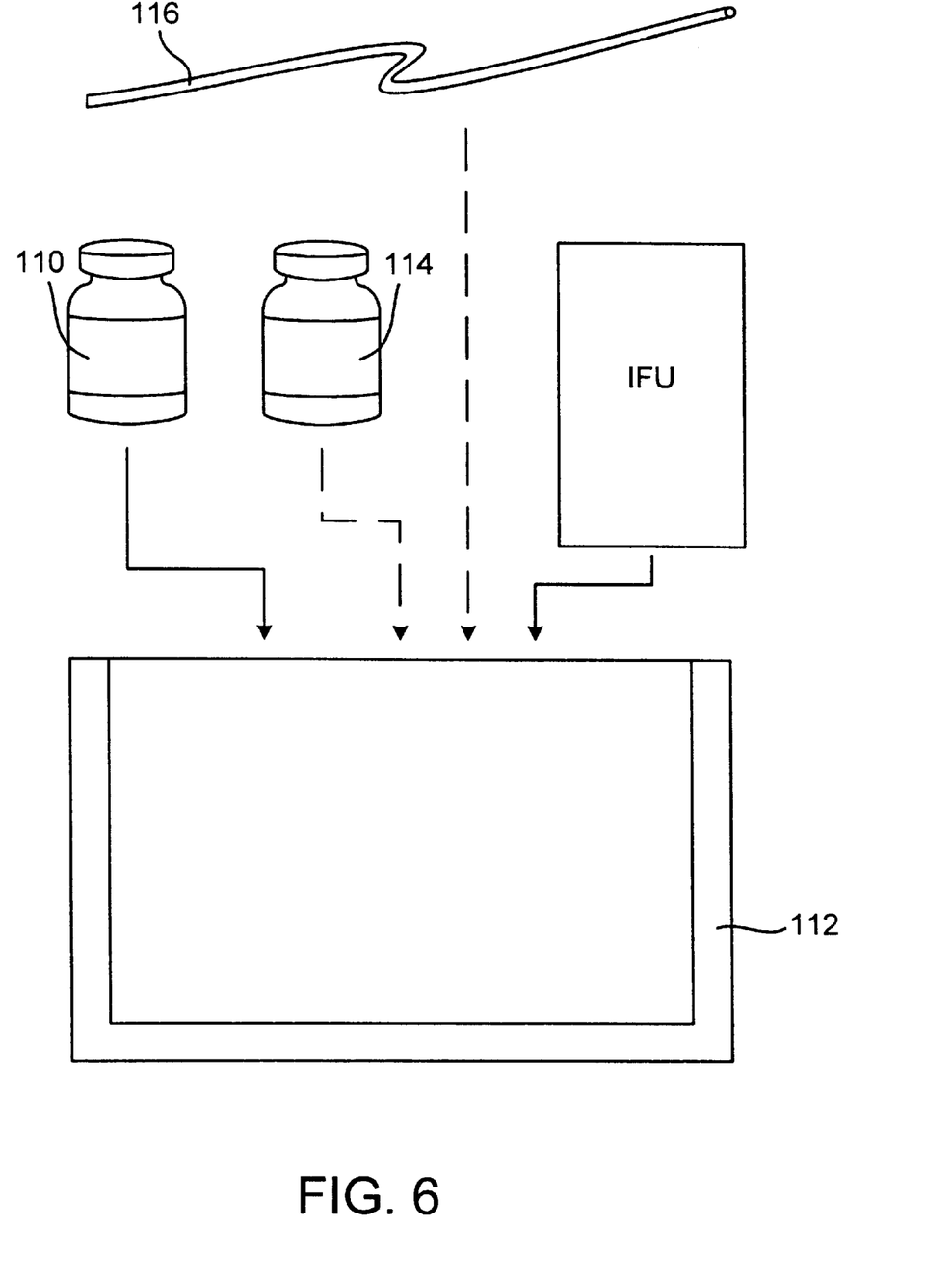
FIG. 6 illustrates a first exemplary kit constructed in accordance with the principles of the present invention.

As illustrated in FIG. 6, a kit according to the present invention comprises a labelling reagent 110 typically packaged with instructions for use IFU in a conventional assay package 112, such as a box, bottle, tube, pouch, or the like. The instructions for use may be written out on a separate instruction sheet or may be partially or fully incorporated onto the packaging materials. The kit will optionally further comprise a keratinolytic agent 114.

Alternatively, the kit may comprise the labelling reagent 110 (optionally with the keratinolytic agent 114) in a package as set forth above. The package will further include an access device 116 capable of being introduced through the ductal orifice, such as a catheter, a fiber optic scope, or the like. Suitable catheters and fiber optic scopes are described in the background art discussed above. Such kits may further comprise instructions for use (IFU) setting forth any of the methods described above.

Figure 7:
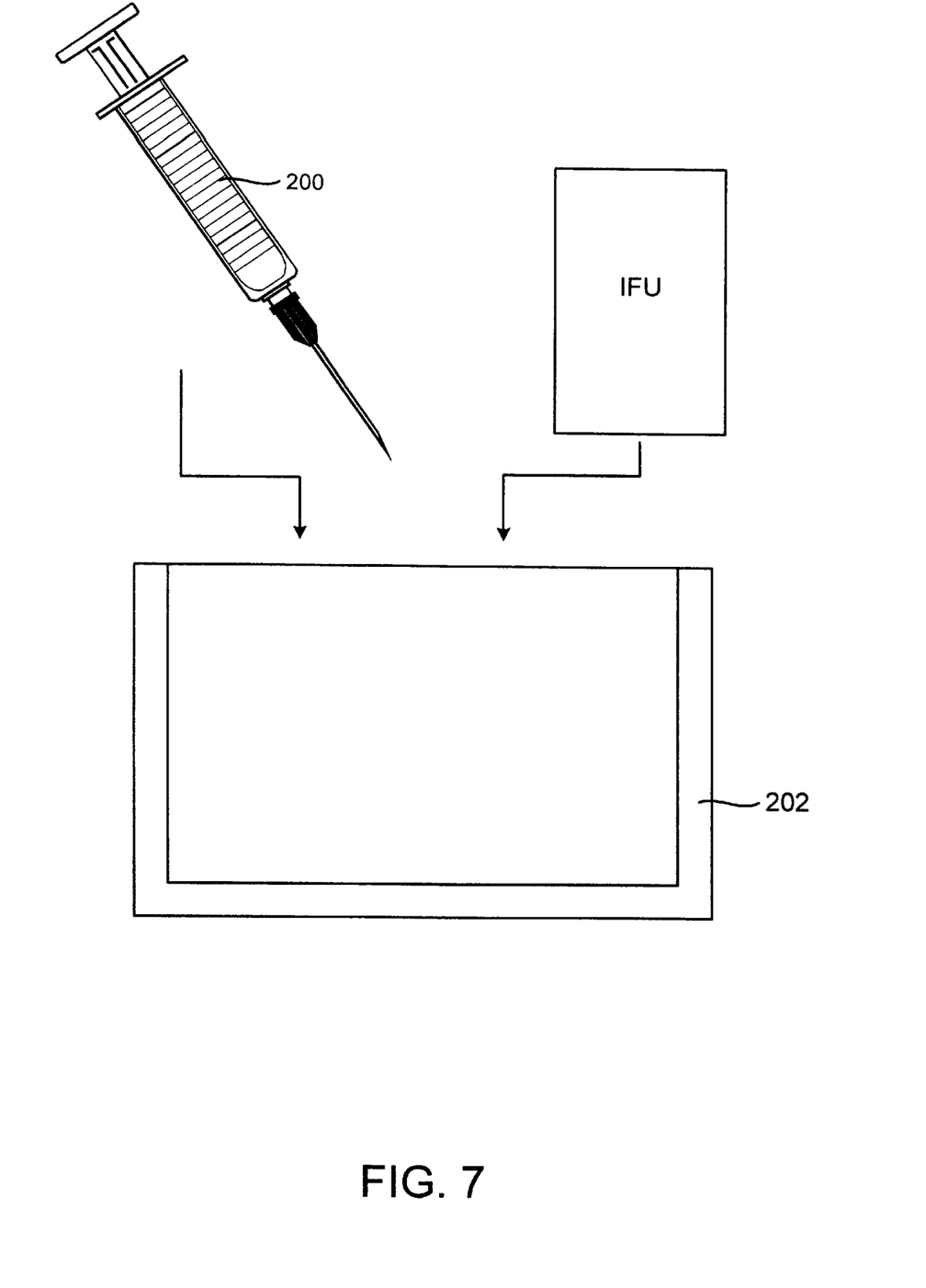
FIG. 7 illustrates a second exemplary kit constructed in accordance with the principles of the present invention.

Referring now to FIG. 7, yet another example of a kit constructed in accordance with the principles of the present invention will be described. The kit of FIG. 7 comprises a needle and syringe 200 which will contain a dye intended to be injected into the base of a nipple according to the methods described above. The kit of FIG. 7 further comprises instructions for use IFU and usually a package 202 which is intended to hold both the needle and syringe and instructions for use. Optionally, the syringe may be packaged without the dye, in which case the dye will typically be provided in a separate reagent container (not illustrated). Also optionally, all or a portion of the instructions for use may be printed on the packaging material itself.

The following experimental descriptions are offered by way of illustration, not by way of imitation.

EXPERIMENTAL

A. Dekeratinizing the Nipple

Acetic acid is mixed with Velvacrol (50% v/w), a pharmaceutical vehicle comprising an aqueous mixture of petrolatum/mineral oil, acetyl alcohol, sodium laural sulfate, cholesterol, methylparaben, butylparaben, and propylparaben. To keep the acetic acid in solution, methyl cellulose (100 mg) is pre-added to the Velvacrol (5 g). The mixture possesses a uniform pasty consistency and is applied to the nipple as an ointment or paste. The keratinolytic agent is typically left on the nipple for twenty-four hours or longer to remove the keratin plugs from the ductal orifices.

B. Labelling of the Ductal Orifice

For cytoplasmic antigens, the ductal epithelium must be solubilized with 70% by weight ethanol. For a membrane or surface antigen, the solubilization step is not necessary. A mouse monoclonal primary antibody is used as a dilution of 1:5 to 1:100 and maintained on the nipple for one hour at room temperature. After such incubation, the nipple is washed with phosphate buffered saline PBS and a secondary antibody (fluoresceinated goat anti-mouse antibody) used at a dilution of from 1:5 to 1:1000 fold at room temperature. After washing with PBS, the nipple may be examined under ultraviolet (UV) light at a wavelength selected for the particular fluorochrome being used. A control can then be run using an antibody of a similar class, but without specificity for any of the ductal epithelial or other markers which may be present on the nipple. This method will provide successful labelling of the ductal orifices and permit subsequent cannulation and examination of each orifice.

C. Ductoscopy

Duct cannulation and exploration can be performed under white (visual) light. One or more ducts are cannulated first with a rigid metal duct-probe (6 Fr Taber-Rothschild Galactography Kit, Manan Medical Products Inc., Northbrook, Ill.) dilated to 0.45 mm to 0.5 mm. A guide wire (0.4 mm) is then inserted, and a catheter passed over the guide wire. Physiological saline (0.2 ml to 0.5 ml) is instilled to wash the duct lumen. The washings may be spun down and analyzed cytologically.

The duct lumen is then dried by injecting 0.2 ml to 0.5 ml air. At the end of the final insufflation, the orifice is held shut by pinching the end of the nipple. An endoscope (FVS-3000, M&M Company, Tokyo), which is 0.4 mm in outer diameter is then threaded into the duct orifice while dilation of the duct with air is maintained. After the endoscope is inserted for 5 mm to 10 mm, its position may be confirmed. The cannulization may then be continued as far distally as possible. Desired diagnostic, therapeutic, or other material may then be instilled into the duct.

Alternatively, after cannulation, the duct may be dilated with saline using a closed system with a burst adapter to allow a better view.

In a particular aspect of the present invention, cells may be removed through the cannula (as washings). The collected cells may be processed according to standard cytological methods for similar washings, such as bronchial washings and biopsy specimens. The cells may be identified directly or indirectly by histopathological analysis of the duct from which the cells were obtained.

Although the foregoing invention has been described in detail for purposes of clarity of understanding, it will be obvious that certain modifications may be practiced within the scope of the appended claims.

What is claimed is:

1. A method for labelling at least one orifice of a breast duct, said method comprising:

treating a nipple to expose tissue at at least one ductal orifice; and exposing the treated nipple to a labelling reagent capable of specifically binding to a tissue marker characteristic of the tissue at the ductal orifice, wherein the labelling reagent binds to the tissue at the orifice but not to other tissues on the nipple.

2. The method as in claim 1, wherein the treating step comprises washing the nipple with a keratinolytic agent.

3. The method as in claim 1, wherein the tissue marker is characteristic of ductal epithelium which extends to the orifice.

4. The method as in claim 3, wherein the marker is selected from the group consisting of cytokeratins, cadhedrins, and epithelial membrane antigens.

5. The method as in claim 1, wherein the labelling reagent comprises a labelled antibody specific for the tissue marker.

6. The method as in claim 5, wherein the antibody is labelled with a label selected from the group consisting of fluorescent labels, dye labels, and chemiluminescent labels.

7. The method as in claim 1, further comprising introducing a ductal access device through at least one labelled orifice.

8. The method as in claim 7, further comprising introducing the ductal access device through a plurality of labelled orifices.

9. The method as in claim 7, wherein the ductal access device is a catheter or a fiberoptic viewing scope.

* * * * *